United States Patent
Gauthier et al.

(10) Patent No.: US 9,855,588 B2
(45) Date of Patent: Jan. 2, 2018

(54) METHOD FOR SORTING SPENT CATALYST AS A FUNCTION OF THE METALS OF THE CATALYST

(71) Applicant: IFP Energies Nouvelles, Rueil-Malmaison (FR)

(72) Inventors: Thierry Gauthier, Brignais (FR); Charles Philippe Lienemann, Villemoirieu (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 0 days.

(21) Appl. No.: 15/101,470

(22) PCT Filed: Dec. 1, 2014

(86) PCT No.: PCT/EP2014/076151
§ 371 (c)(1),
(2) Date: Jun. 3, 2016

(87) PCT Pub. No.: WO2015/082424
PCT Pub. Date: Jun. 11, 2015

(65) Prior Publication Data
US 2016/0318073 A1    Nov. 3, 2016

(30) Foreign Application Priority Data
Dec. 6, 2013   (FR) ...................................... 13 62225

(51) Int. Cl.
*B07C 5/00* (2006.01)
*B07C 5/342* (2006.01)
(Continued)

(52) U.S. Cl.
CPC ........... *B07C 5/3427* (2013.01); *B01J 23/888* (2013.01); *B01J 23/94* (2013.01); *B01J 23/96* (2013.01);
(Continued)

(58) Field of Classification Search
CPC ........ B07C 5/342; B07C 5/3427; B01J 23/94; B01J 23/96; B01J 23/888
(Continued)

(56) References Cited

U.S. PATENT DOCUMENTS

| | | | | |
|---|---|---|---|---|
| 5,751,416 A | * | 5/1998 | Singh | ........................ G01J 3/30 356/300 |
| 6,407,811 B1 | * | 6/2002 | Snyder | .................... G01J 3/443 356/316 |

(Continued)

FOREIGN PATENT DOCUMENTS

| | | |
|---|---|---|
| EP | 2008726 A1 | 12/2008 |
| FR | EP 2008726 A1 * 12/2008 | ........... B07C 5/3427 |
| WO | 2013013276 A1 | 1/2013 |

OTHER PUBLICATIONS

International Search Report dated Jan. 9, 2015 issued in corresponding PCT/EP2014/076151 application (pp. 1-3).

*Primary Examiner* — Terrell Matthews
(74) *Attorney, Agent, or Firm* — Millen White Zelano and Branigan, PC; John Sopp; Csaba Henter

(57) ABSTRACT

A method and device for separating at least one catalyst from a mixture of homogeneously shaped catalysts, the catalysts comprising at least one metal selected from the group formed by Ni, Co, Mo, W, the catalyst to be separated comprising a characteristic metal selected from the group formed by Ni, Co, Mo, W and the other catalysts of the mixture not containing said characteristic metal, in which method:
  the grains of the catalyst of said mixture pass in front of the LIBS detection system,
  the presence of said characteristic metal in the catalysts is detected by the LIBS technique, the wavelength being selected so as to detect said characteristic metal,
(Continued)

the LIBS detection system sends a signal to a means for evacuating grains of catalyst to be separated in a manner such as to separate said grains from the other catalysts of said mixture.

19 Claims, 2 Drawing Sheets

(51) Int. Cl.

| | |
|---|---|
| *B01J 23/888* | (2006.01) |
| *G01N 21/71* | (2006.01) |
| *B01J 35/02* | (2006.01) |
| *C10G 45/00* | (2006.01) |
| *C10G 47/00* | (2006.01) |
| *C10G 45/08* | (2006.01) |
| *C10G 45/12* | (2006.01) |
| *C10G 47/20* | (2006.01) |
| *B01J 38/72* | (2006.01) |
| *B01J 23/94* | (2006.01) |
| *B01J 35/00* | (2006.01) |
| *B01J 23/96* | (2006.01) |
| *B01J 29/90* | (2006.01) |
| *B01J 23/75* | (2006.01) |
| *B01J 23/755* | (2006.01) |
| *B01J 23/28* | (2006.01) |
| *B01J 23/30* | (2006.01) |
| *B01J 23/882* | (2006.01) |
| *B01J 23/883* | (2006.01) |
| *B01J 29/072* | (2006.01) |
| *B01J 29/076* | (2006.01) |
| *B01J 38/68* | (2006.01) |

(52) U.S. Cl.
CPC ........... *B01J 29/90* (2013.01); *B01J 35/0006* (2013.01); *B01J 35/026* (2013.01); *B01J 38/72* (2013.01); *B07C 5/342* (2013.01); *C10G 45/00* (2013.01); *C10G 45/08* (2013.01); *C10G 45/12* (2013.01); *C10G 47/00* (2013.01); *C10G 47/20* (2013.01); *G01N 21/718* (2013.01); *B01J 23/28* (2013.01); *B01J 23/30* (2013.01); *B01J 23/75* (2013.01); *B01J 23/755* (2013.01); *B01J 23/882* (2013.01); *B01J 23/883* (2013.01); *B01J 23/8885* (2013.01); *B01J 29/072* (2013.01); *B01J 29/076* (2013.01); *B01J 38/68* (2013.01); *B07C 2501/0018* (2013.01)

(58) Field of Classification Search
USPC .................................. 209/576, 577, 579, 580
See application file for complete search history.

(56) References Cited

U.S. PATENT DOCUMENTS

| | | | | |
|---|---|---|---|---|
| 7,530,265 | B2* | 5/2009 | DiFoggio | E21B 47/102 73/152.42 |
| 7,763,820 | B1* | 7/2010 | Sommer, Jr. | B07C 5/346 209/576 |
| 8,307,985 | B2* | 11/2012 | Dufresne | B07C 5/3427 209/11 |
| 8,855,809 | B2* | 10/2014 | Spencer | B07C 5/3416 378/53 |
| 2006/0258531 | A1* | 11/2006 | Koyama | B01J 23/85 502/337 |
| 2007/0296967 | A1* | 12/2007 | Gupta | G01J 3/2889 356/318 |
| 2009/0000992 | A1 | 1/2009 | Dufresne et al. | |
| 2013/0079918 | A1* | 3/2013 | Spencer | B07C 5/3416 700/223 |
| 2013/0264249 | A1* | 10/2013 | Sommer, Jr. | B07C 5/346 209/589 |
| 2014/0260801 | A1* | 9/2014 | Wellwood | B07C 5/3427 75/392 |
| 2015/0314332 | A1* | 11/2015 | Dimitrakis | G01N 33/24 209/10 |
| 2016/0078678 | A1* | 3/2016 | Hotte | G06Q 10/06311 705/7.13 |
| 2016/0161415 | A1* | 6/2016 | Robinson | G01N 21/67 435/7.2 |

\* cited by examiner and a device for separating at least one catalyst from a mixture of homogeneously shaped catalysts, the catalysts comprising at least one metal selected from the group formed by Ni, Co, Mo, W.

More particularly, the invention relates to a method and a device which can be used to sort and separate catalysts containing tungsten from other catalysts which are devoid of tungsten but contain molybdenum.

PRIOR ART

U.S. Pat. No. 7,886,915 describes a method for the in-line sorting of metal scrap (scrap iron, ferrous and non-ferrous chips). The proposed system is an in-line analytical system for determining the chemical composition of the elements to be sorted. In that invention, the materials to be sorted are metal parts with a variable shape and size which is not determined. One of the aspects of the invention concerns employing bulk analysis; the particles are not analysed individually. The envisaged industrial application concerns recycling scrap iron which is subsequently smelted in electric furnaces, and so it is important to the final quality of the steel to eliminate non-ferrous metals, in particular copper, as far as possible.

Patent application US 2013/0073077 A1 concerns a sorting system adapted to ores. Many types of analytical means are associated with the proposed sorting system; they preferably concern Near Infra Red (NIR) or LIBS (Laser Induced Breakdown Spectroscopy), X-ray or magnetic detector techniques.

Here again, the size of the particles is not defined, since the ore to be sorted results from an initial grinding or crushing process. An ore contains metallic elements which are mixed with rock the crystalline forms and chemical composition of which may vary. The concentration of metals is variable from one particle to another. In that type of application, in general the particles are sorted in order to retain those in which the composition of the desired metallic element is the highest.

Patent application WO 2013/013276 A1 also describes a sorting system adapted to ores in a similar context to patent application US 2013/0073077 A1. The shape and size of the elements to be sorted is variable, as is also their composition since it is applied to ores. An arrangement of particles on the conveyor belt is claimed in order to allow the particles to be sorted. In particular, the spacing between the various particles on the conveyor belt of the sorting line is controlled. Preferably, a system for arranging in rows transverse to the direction of movement on the belt is proposed.

Finally, in application WO2012/168938 A1, a sorting system is proposed which here again is preferably applied to the sorting of ores, with a strong quantitative aspect which means that a rejection threshold can be set based on a minimum content of one of the desired elements. The in-line detection means are based on two lasers and a double pulsing system, which means that an absorption reading can be obtained which differs from the emission reading conventionally used in the LIBS technique.

Patent application US 2013/264249 describes a method for sorting objects containing recyclable materials using X ray fluorescence.

All of these techniques have been developed in the mining context, employing coarse sorting.

Sorting catalysts requires a more accurate approach in order to ensure that the maximum amount of metals is recovered given their high price.

Patent EP-2 008 726 proposes colour sorting spent catalysts as a function of their surface shades of grey.

These catalysts may, for example, be partially mixed following operations for discharging reactors containing beds of catalysts with different compositions.

This case is primarily encountered in hydrocracking reactors containing at least one bed of hydrotreatment catalyst (containing Ni and/or Co and/or Mo but devoid of W) and at least one bed of hydrocracking catalyst (containing W) or containing at least one bed of hydrotreatment catalyst (containing W) and at least one bed of hydrocracking catalyst (containing Ni and/or Co and/or Mo but devoid of W). In general, discharging the beds cannot completely separate the catalysts. This is the case, for example, with NiW catalysts present in a mixture of NiMo, CoMo or NiCoMo catalysts.

However, tungsten is difficult to extract in the presence of Mo, necessitating a series of expensive treatments. The separation of catalysts containing W and catalysts containing Mo would mean that less expensive conventional techniques could be used.

The invention overcomes these disadvantages. It can be used to separate catalysts from mixtures of hydrotreatment and/or hydrocracking catalysts. It can also be used to separate catalyst containing metals which cannot easily be reprocessed in the presence of other metals contained in other catalysts.

Thus, the subsequent treatment (which will be termed reprocessing) of catalysts using conventional treatment pathways to separate and recover the metals is facilitated by the absence of certain elements.

Thus, more precisely, the invention concerns the sorting of mixtures of hydrotreatment and/or hydrocracking catalysts containing W and/or Ni and/or Co and/or Mo.

It is particularly suitable for sorting catalysts containing tungsten (such as NiW) present in a mixture with catalyst containing Ni and/or Co and/or Mo but devoid of W (for example NiMo, CoMo or NiCoMo metal-containing catalysts).

A supplemental difficulty overcome by the method of the invention resides in the fact that it can be used to work on spent catalysts the surface and pores of which are loaded with carbon. Another advantage of the invention is that the catalysts may originate from different sources, and thus may have different compositions and contents.

However, it should be noted that the invention is also applicable to both fresh and regenerated catalysts.

Fresh catalyst, when this is used, will have been sulphurized in order to convert the metallic oxides into sulphides. The catalyst is then used in the process for one or more cycles of operations. The spent catalyst may be regenerated, in general ex situ, between the operation cycles in order in particular to eliminate elements such as coke which cause deactivation of the catalyst.

At the end of the cycles of operation, the catalyst is spent and can no longer be regenerated due, for example, to degradation of the mechanical properties of the catalyst or sintering of the active phases.

Recovery and separation of the various constituents (in particular metals) of which the catalyst is composed and recycling them to produce other catalysts or to supply other sectors such as the steel industry is desirable.

Reprocessing may be carried out using hydrometallurgy: acid or basic attack of the catalysts in order to dissolve the constituents which are then separated by controlled chemical precipitation, by physical separation such as adsorption, or by other means such as electrodeposition.

Thus, a method for separating these catalysts has been developed.

The invention concerns a method for separating at least one catalyst from a mixture of homogeneously shaped catalysts, the catalysts comprising at least one metal selected from the group formed by Ni, Co, Mo, W, the catalyst to be separated comprising a characteristic metal selected from the group formed by Ni, Co, Mo, W and the other catalysts of the mixture not containing said characteristic metal, in which method:
 - the grains of the catalyst of said mixture pass in front of the LIBS detection system,
 - the presence of said characteristic metal in the catalysts is detected by the LIBS technique, the wavelength being selected so as to detect said characteristic metal,
 - the LIBS detection system sends a signal to a means for evacuating grains of catalyst to be separated in a manner such as to separate said grains from the other catalysts of said mixture.

The method is of particular advantage when the catalyst to be separated contains tungsten as the characteristic metal, the other catalysts of the mixture being devoid of tungsten and said other catalysts containing at least one metal selected from the group formed by Ni, Co, Mo.

Even more advantageously, the catalyst to be separated contains tungsten as the characteristic metal, the other catalysts of the mixture being devoid of tungsten and at least one of said other catalysts containing molybdenum.

In general, the catalyst to be separated contains W as the characteristic metal and also contains Ni, the other catalysts of the mixture contain NiMo or CoMo or NiCoMo and are devoid of W.

The method is of particular advantage when the catalysts of the mixture are spent catalysts. The method is applicable to fresh or regenerated catalysts.

The catalysts of the mixture are often hydrotreatment and/or hydrocracking catalysts. In particular, they are spent hydrotreatment and/or hydrocracking catalysts the support of which is based on (and preferably constituted by) alumina or silica-alumina, with zeolite optionally being present.

In accordance with the invention, the catalysts are homogeneously shaped, preferably in the form of cylindrical extrudates, beads, trilobes or multilobes. The cylindrical extrudate shape is particularly preferred. Trilobe or multilobe shapes are also suitable for this method.

In accordance with the invention, the time period for one grain to pass in front of the LIBS detection system is less than 50 ms, preferably less than 10 ms.

Preferably, the grains flow in a manner such that they are spaced apart by a distance in the range from zero to their largest characteristic dimension, the measurement frequency being in the range 1/t to 1/2t, t being the period of time for a grain to pass in front of the LIBS detection system. Preferably, the grains are cylindrical extrudates.

Advantageously, the maximum spacing between the grains is equal to their largest characteristic dimension.

Advantageously, the detection system is positioned in a manner such that the depth of the analysis field above the surface of the transport means is in the range ⅓ to 3 times the smallest characteristic dimension of the grain.

For catalysts which are homogeneously shaped items with a well-defined shape (cylindrical extrudates, trilobes or multilobes, beads), the aim of the invention is to propose a sorting method based on the very rapid in-line LIBS detection method.

A particular aim of the invention is the provision of a method for separating grains of hydrotreatment and hydrocracking catalysts containing tungsten from other catalysts which contain molybdenum but which are devoid of tungsten.

In a preferred embodiment, the invention concerns a method for separating grains of hydrotreatment catalyst containing tungsten. The support is generally constituted by alumina or silica-alumina. The tungsten is frequently associated with nickel.

In another preferred embodiment, the invention concerns a method for separating grains of hydrocracking catalyst containing tungsten. The support is generally constituted by a silica-alumina, or it is a zeolitic support (i.e. an alumina or silica-alumina support containing a zeolite). The zeolite is generally Y zeolite. The tungsten is often associated with nickel.

In general, the invention concerns a method for eliminating particles containing a predetermined metal (termed the characteristic metal, such as W) in a batch of catalyst the grains of which are homogeneous in shape.

The analysis method is thus used solely to detect the presence of this characteristic metal. In general, in fresh catalysts, the minimum characteristic metal content in the catalyst grain is 1% by weight. The characteristic metal wavelength is selected to be that at which the properties of the support (composition, presence of pollutants or of other metallic elements, etc.) have no influence. This is made possible because quantitative analysis is not useful for this type of sorting.

The premise is solely the presence or absence of this characteristic metal in order to optimize the sorting and detection means. Preferably, a grain-by-grain type of sorting over the entire batch is sought. The detection speed is high in order to allow the grains to run past the detector rapidly and to allow for a high sorting capacity. The fixed geometric characteristics of the grains of catalyst means that the arrangement of the grains on the transport means of the sorting line can be optimized.

The Catalysts:

The catalysts are articles with a well-defined shape and composition.

The catalysts are homogeneously shaped, preferably in the form of cylindrical extrudates, beads, trilobes or multilobes.

Thus, the mixture of catalysts is homogeneously shaped. This means, for example, that all of the catalysts have the same shape: they can be in the form of cylindrical extrudates, for example. Catalysts with the same shape may differ in size.

In general, the catalyst is shaped into the form of extrudates said to be cylindrical, with a diameter which is often in the range 0.5 to 3 mm (often close to 0.9-1.5 mm) and with a length equal to 3 to 15 times the diameter of the extrudates. It may be in the shape of beads 0.5 to 20 mm in diameter, or pellets. The catalysts may also be used in the form of dispersed powders with a diameter which is in general less than 200 microns, but this shaping is of no relevance to the invention. The catalyst is generally used in the form of extrudates, trilobes or multilobes, usually in the form of extrudates.

The size of the particles is generally well-defined and the dispersion of the geometrical properties is generally small compared with its mean value.

In the remainder of the text, the largest characteristic dimension of the grain will be termed the length in the case of an extrudate, the diameter in the case of a bead or pellet, and the length in the case of a trilobe or a multilobe. This value is given by the manufacturer of the fresh catalyst. When the catalysts are regenerated or spent catalysts, this value is determined by the operator from measurements or statistics on sample(s) of the batch to be treated.

In the same manner, the smallest characteristic dimension corresponds to the diameter for a bead or an extrudate and for a multilobe, to the diameter of the circle circumscribing the tangents to the crests of the lobes.

During discharge and/or regeneration and despite all the precautions which are taken, catalyst grains break and fines are formed under the effect of wear. A size distribution around the characteristic dimension of the grain is produced. The operator could determine this distribution from measurements on a sample of the batch to be treated. In this case, the value for the largest characteristic dimension of the grain (for example the length) which is used corresponds to 10% of the distribution. This means that 10% of the grains have dimensions too far from the mean distribution value and are not considered in the determination. Clearly, this limit of 10% could be adjusted as required; it could be 15%, 20%, etc., or less (for example 5%), depending on the physical condition and sizes of the batch to be treated.

Another possibility is to carry out a mechanical separation of grains with a dimension below the desired dimension (fines, for example) and to treat the resulting batch.

The catalyst comprises a support with a well-defined texture and composition and at least one metal selected from Ni, Co, Mo, W.

The support is generally based on alumina or silica-alumina with the optional presence of zeolite. More generally, it is constituted by alumina or silica-alumina with the optional presence of zeolite.

The metals such as Ni, Mo, Co, W are dispersed in or on the support, usually by impregnation, or by any other technique known to the person skilled in the art.

Hydrotreatment and hydrocracking catalysts are catalysts based on sulphides of cobalt, nickel, molybdenum or tungsten which are supported, generally on alumina. The fresh catalyst is initially prepared with the oxides of these metals which are then sulphurized. Depending on the aims of the reaction, CoMo, NiMo, NiCoMo or NiW combinations are generally used.

The initial composition of nickel or cobalt oxide is generally in the range 2% to 10% by weight on the catalyst, and the composition of molybdenum and tungsten is close to 15% to 30% by weight. The quantity of metals in the catalysts is not limiting for carrying out the invention, provided that the characteristic metal can be detected by the LIBS technique.

After use in the processes, the catalyst may contain external elements which are deposited during the operation, usually carbon, sulphur and nitrogen.

The invention is particularly suitable in the context of sorting hydrotreatment or hydrocracking catalysts in the extruded, trilobe or multilobe form, in particular in the extruded form.

Detection Using the LIBS Technique

The LIBS technique can be used to focus and localise detection in order to render it more effective.

It is an elemental analysis technique which is increasingly being used for the direct analysis of solids and liquids. The increasing interest in this technique derives from its many advantages, including minimal sample preparation, rapid in situ analysis, and ease of use.

The principle resides in focussing a pulsed laser onto the surface of the sample. This focussing of the laser pulse lasting a few nanoseconds or even femtoseconds and with an energy of the order of a few tens of millijoules onto the point to be analysed on the material causes the formation of a micro-plasma. This micro-plasma is a reflection of the composition of the surface of the sample, which generates vaporization and ionization of the material, then cools over time.

The size of the point for analysis is usually of the order of a few microns, or even about ten microns. As they de-excite, the atoms and ions of the material present in the micro-plasma emit photons with a wavelength which is characteristic of the chemical element. A spectrometer in the UV/visible range collects and interprets the light emitted by the plasma. The emission lines generated by the sample being analysed can be used to identify the elements present in the sample (qualitative analysis), and thus the chemical species which make up the sample will be known. Their intensity may also be measured and compared with that measured for a range of samples of known concentration in order to measure the elemental composition of the sample (quantitative analysis).

In the case of the present invention, a qualitative analysis can be used to detect the presence or absence of metal in the catalyst which is to be separated, such as tungsten.

The rapidity of the LIBS response is an essential advantage for sorting productivity.

The grains of catalyst are irradiated by laser. In turn, the associated emission is analysed by spectroscopy at a wavelength selected to allow detection of the characteristic metal of the catalyst to be separated.

As an example, for tungsten, many atomic or ionic emission lines located between $\lambda=207$ and 430 nm may be suitable, for example. Preferably, the line at a wavelength of 400.875 nm is used because of its high intensity and its absence of interference with Co, Ni, Mo, Al and Si.

Depending on the elements present in the catalyst, the line at 297.971 nm may also be used. The lines at 270.880 and 309.350 nm are less intense, but may also be used. The lines at 239.709, 207.911, 220.448 and 224.875 nm may also be used, but the presence of Ni, Co or Mo or other elements should be verified upstream in order to determine whether the resolution of the spectrometer is sufficient to discriminate the lines of these various elements.

The detection system is preferably adjusted so that the depth of focus for the analysis above the surface of the transport means is in the range ⅓ to 3 times the smallest characteristic dimension of the grain of catalyst (the diameter of the extrudate in the case of a substantially cylindrical particle, the diameter of the grain in the case of a spherical particle), in order to allow ultrafast detection of the composition of the grains.

Since the grains are homogeneous in shape and the analysis is qualitative (detection of the presence or absence of a constituent present in a concentration of at least 1% by weight), it is not necessary to vary the focus, which saves time.

In practice, the analyser can be used to determine the composition of the desired element with a response time "t" of less than 50 ms, preferably less than 10 ms.

Thus, the time period for one grain to pass is less than 50 ms, preferably less than 10 ms.

In a preferred embodiment of the invention, the grains of catalyst are spaced apart, preferably regularly, by a maximum distance corresponding to the largest characteristic dimension of the grains of catalyst, as defined above.

The detection measurement is repeated at intervals of time.

When the grains are spaced apart by their largest characteristic dimension, the frequency of measurement is equal to 1/2t, with t being the period of time for a grain to pass in front of the detection system. When the grains flow in a contiguous manner (the grains are contiguous when their spacing is equal to zero), the frequency is equal to 1/t.

More generally, the grains, preferably cylindrical extrudates, flow in a manner such that their spacing is in the range from zero to their largest characteristic dimension, and the frequency of measurement is in the range 1/t to 1/2t, t being the period of time for a grain to pass in front of the LIBS detection system.

The spacing between the grains is controlled by means which are regulated as a function of the detection time of the LIBS detection system.

As an example, they are means for controlling the supply (rate of flow) of the grains of catalyst onto the transport means (band conveyor, etc.) and the speed of said means. In a preferred embodiment of the invention, each grain of catalyst is exposed to the detection system. When the grains have substantially identical contents of the same characteristic metal, it is possible to process small batches of grains of catalyst.

Grain Separation

When the LIBS detection system detects the characteristic metal in one or more grains, it sends a signal to a means for evacuating grains of catalyst to be separated so as to separate said grains from other catalysts of said mixture.

The detection system is connected to a system for controlling the means for evacuating the grains containing the desired characteristic metal (such as tungsten). These means are located at the transport means (conveyor belt, etc.), and they are usually located at the downstream (outlet) end of the transport means.

These means are actuated with a temporal offset which is a function of their distance from the detection system.

As an example, if the grain of catalyst contains the desired characteristic metal, then the means are actuated and can deflect the flow of the grain towards a receptacle A. If the catalyst does not contain the desired metal, then the means are not actuated and the catalyst flows normally towards another receptacle B.

In the case in which several catalysts have to be separated, several LIBS detection systems are advantageously provided, each with a wavelength which is adapted to the characteristic element to be separated. The evacuation means are adapted accordingly.

The method of the invention has been described starting from a catalyst to be separated (such as NiW), but the wavelength could equally be adjusted to Mo, which would also result in separating catalysts containing Mo from those containing W. The characteristic metal would then be Mo.

The invention also concerns a device for separating at least one catalyst from a mixture of homogeneously shaped catalysts, the catalyst to be separated comprising a characteristic metal and the other catalysts of the mixture not containing said characteristic metal, said device comprising:

a line for transporting the mixture of catalysts, provided with a transport means, means for controlling the rate of flow of the grains onto said means and means for controlling its speed, said means being regulated in a manner such that the maximum distance between the grains is equal to the largest characteristic dimension of a grain and in that the period of time for a grain to pass in front of the LIBS detection means is less than 50 ms, preferably less than 10 ms, a LIBS detection system comprising at least one laser in front of which the grains pass, the detection time being less than 50 ms, preferably less than 10 ms, and the wavelength being that of the characteristic metal, at least one analyser (8) and at least one control means (10), at least one means for evacuating grains of catalyst to be separated and at least one means for evacuating grains of the other catalysts, said means being actuated from said control means when the characteristic metal is detected.

Advantageously, the transport means is a band conveyor (or conveyor belt). This may also be a die provided with an endless screw with a hollow axle provided with at least one opening adapted for detection and at least one opening adapted for separation of the grains of catalyst.

Preferably, the transport means is a conveyor belt which is preferably ribbed, the depth of the ribs being in the range 0.7 to 1.3 times the smallest characteristic dimension of the grains, corresponding to the diameter in the case of a sphere or an extrudate.

Preferably, said means of the transport line are adjusted in a manner such that the grains flow with a spacing in the range from zero to their largest characteristic dimension, the measurement frequency being in the range 1/t to 1/2t, t being the period of time for a grain to pass in front of the LIBS detection system.

The grains are preferably cylindrical extrudates, trilobes or multilobes.

When the grains are spaced apart by their largest characteristic dimension, the frequency of measurement is equal to 1/2t, with t being the period of time for a grain to pass in front of the detection system. When the grains flow in a contiguous manner (the grains are contiguous when their spacing is equal to zero), the frequency is equal to 1/t.

The device of the invention is particularly well suited to carrying out the method of the invention. The features described above for the method also apply to the device.

Advantageously, the detection system is positioned in a manner such that the depth of the analysis field above the surface of the transport means is in the range ⅓ to 3 times the smallest characteristic dimension of the grain.

Advantageously, the period of time for a grain to pass in front of the LIBS detection system is less than 50 ms, preferably less than 10 ms, and the analyses being repeated at a time interval which is at most equal to the time taken for the grain with the smallest characteristic dimension to pass.

DETAILED DESCRIPTION OF THE METHOD AND THE SEPARATION DEVICE

The mixture of catalyst initially stored in silos or in sacks is supplied to a catalyst line which advantageously comprises a band conveyor such as a conveyor belt and which comprises means for controlling the flow rate of the grains onto the band conveyor.

The transport means may also be other means such as, for example, a die in which an endless screw with a hollow axle is rotated to cause the grains of catalysts to advance, with openings being provided in the die to allow detection on the one hand and separation of the grains of catalyst on the other hand.

The grains of catalyst are transported in front of the LIBS system for qualitative analysis of the chemical composition in order to determine whether the grains of catalyst contain the characteristic metal. A qualitative analysis is carried out in order to detect the presence of one or more unwanted elements. As an example, the presence or absence of tungsten could be investigated in order to separate grains containing this metal.

Figure 1:
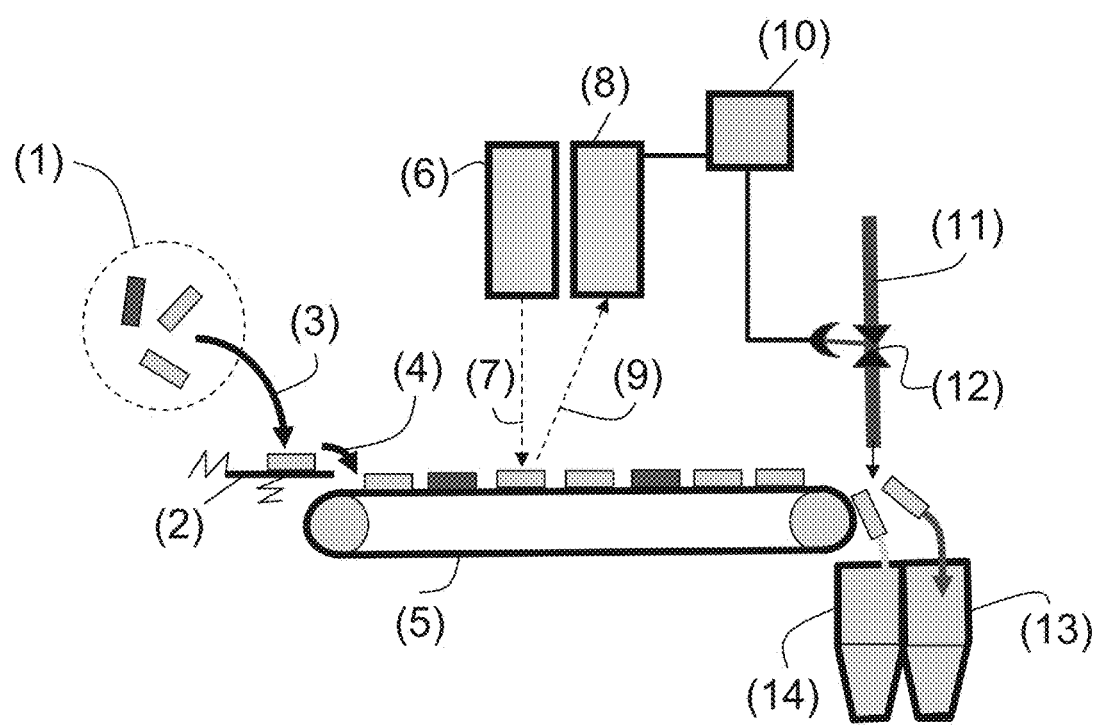
FIG. 1 shows, as an illustration, a preferred but non-limiting embodiment of a method and device of the present invention having a plate, 2, which vibrates in two orthogonal directions.

FIG. 1 shows, as an illustration, a preferred but non-limiting embodiment of the method and device of the present invention.

The mixture of unsorted catalyst 1 is supplied to a means 2 for controlling the rate of flow of the grains onto the band conveyor 5. The means for supplying the mixture 3 may be manual (emptying bags, for example) or automatic (for example, controlled dispensing from a silo).

The invention is described with a band conveyor as the transport means, but the description is entirely applicable to another transport means such as the screw and die described above, for example.

The means for controlling the flow rate are means which are well known to the person skilled in the art such as, for example, inclined vibrating plates, which can distribute the grains of catalyst in a uniform manner and can allow the rate of flow of catalyst on the plate towards the band conveyor to be adjusted. In this manner, the person skilled in the art will be able to adjust the distance between two grains on the transport line and adjust the frequency of detection as a consequence or, conversely, will be able to adjust the distance as a function of the detection frequencies.

By way of example, in FIG. 1, we have represented at 2 a plate which vibrates in two orthogonal directions. With this type of equipment, it is possible to adjust the vibration frequencies in order to modulate the flow rate of solid 4 towards the band conveyor 5, to adjust the distribution between the grains on the cross section of passage and thus to control the spacing between the grains as a function of the rate of displacement of the conveyor.

As an optimum, the device will be adjusted so that the maximum distance between the grains is equal to the largest characteristic dimension of a grain, as defined above.

Figure 2:
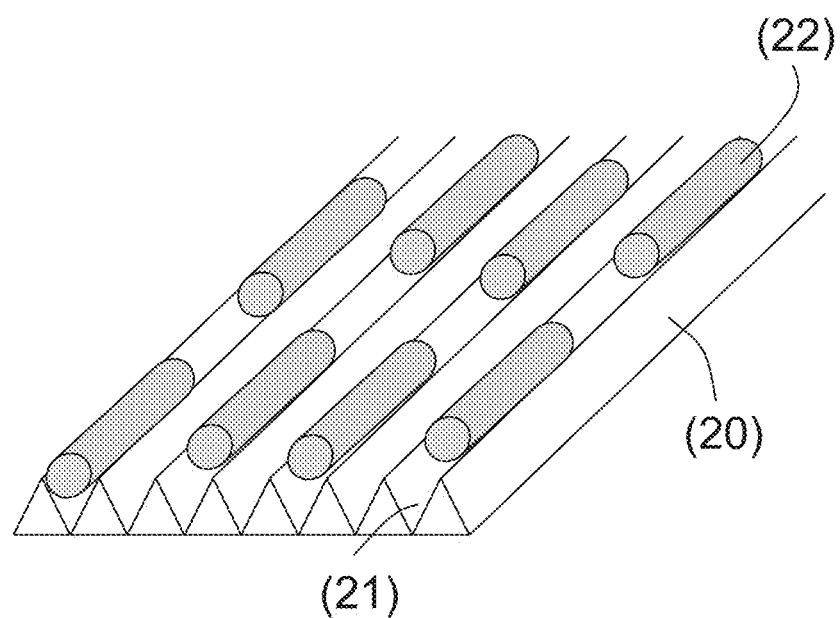
FIG. 2 shows a non-limiting embodiment of a method and device of the present invention wherein the grains of catalyst fall onto a band conveyor which is a ribbed conveyor belt.

At the outlet from the flow rate control means 2, the grains of catalyst fall onto the band conveyor which may be a simple flat conveyor belt or a ribbed conveyor belt, as can be seen in FIG. 2.

The ribbed belt of FIG. 2 is of distinct interest when sorting extrudates (as is the case with catalysts containing tungsten), because it can advantageously be used to orientate the grains of catalyst in the direction of flow. The flow of the catalysts is thus more regular and spaced, which favours detection, and separation and improves the productivity of the facility.

In the case of a ribbed belt 20, a crenellated shape 21 with an equilateral triangular shape as can be seen in FIG. 2 is advantageous; the depth of the ribs on the belt is thus ideally in the range 0.7 times to 1.3 times the largest characteristic dimension of the grains (which is the diameter of the grains of catalyst in the case of extrudates or beads). In the case of trilobes or multilobes, the depth of the ribs on a belt is thus ideally in the range 0.7 times to 1.3 times the largest characteristic dimension of the grains. In this context, the "diameter" and said "dimension" refer to fresh catalysts. In general, the depth is close to said largest dimension (i.e. approximately single-fold).

The grains 22 are positioned on the belt 20. The rate of advance of the belt is adjusted in order to optimize the production capacity on the one hand and on the other hand the capacity of the system to detect the desired characteristic metal in the grains of catalyst.

Preferably, the period of time for one grain to pass is selected so as to be less than 50 ms, and is preferably less than 10 ms. More generally, the period for passage is as short as possible, in alignment with the response time of the detection system.

Under these conditions, for example, for a cylindrical extrudate with a length of 10 mm, the speed of transport of the grains on the band conveyor is more than 0.2 m/s and preferably in the range 0.2 to 10 m/s, the period of time for passing in front of the detection system thus varying between 1 and less than 50 ms.

In the case of a 5 mm extrudate, the speed is preferably in the range 0.1 to 5 m/s.

Since the maximum mean spacing of the grains is their largest characteristic dimension, it is then possible to make these measurements every 1 to less than 50 ms, in alignment with the capacities of the measurement instruments, and thus to carry out the detection on all of the grains of catalyst.

The detection system comprises at least one laser 6, at least one spectrometer (or analyser) 8 and at least one means 10 for controlling the opening or otherwise of at least one evacuation means.

A laser 6 emits a beam which is focussed on the surface of the sample 7. Following a pulse of the order of a femtosecond to a nanosecond between the laser and the sample, a plasma which is a reflection of the composition of the sample is generated and after a few milliseconds, emits at wavelengths which reflect the composition of the sample 9.

The emissions from the sample 9 are analysed by a spectrometer 8 at the wavelengths which are specific to the characteristic metal which is to be detected.

As an example, in order to detect the presence or absence of tungsten in the hydrocracking or hydrotreatment catalysts, the line at a wavelength of 400.875 nm is used because of its high intensity. The line at 297.971 nm may also be used. These two lines can be used to detect the presence of tungsten while minimizing the interference from Ni, Co, Mo, Al or Si.

Depending on requirements, it is possible to analyse all of the grains passing in front of the detection system 6-7-8-9 on the band conveyor 5, overall or individually, by using several laser systems 6 in parallel so as to cover the width of the band conveyor and also by adapting or decoupling the laser and the spectrometer 8 analysing the emissions 9.

It is also possible to elect to operate statistically by analysing only a fraction of the flow or to consider displacing the lasers 6 and the spectrometer(s) 8 across the width.

The detection system, and more precisely the spectrometer 8, is connected to control means 10 which can be used to convert the results of the analysis into an action in order to actuate said evacuation means (in this case the valve 12).

These means are, for example, constituted by a computer which can be used to trigger opening of a valve 12.

As an example, when the analyser 8 detects the presence of the desired element in a grain of catalyst, it sends a signal to the control means 10 which actuates opening of the valve 12.

This is located on a line of inert fluid (for example air) under a pressure, if possible, of more than 5 bars (preferably with air) in order to favour the generation of a jet of gas (air) which is sufficient to evacuate the grain.

The valve 12 opens for a predetermined period DT1, then closes automatically. Opening of the valve means that a jet can be generated at the lower end of the line 11. It acts with the line as a nozzle for ejecting gas (air).

Advantageously, the line 11 is positioned at the end of the conveyor belt at a distance of at most 10 cm from the end of the belt (depending on the speed of advance of the belt; the lower the speed of advance of the belt, the closer the line 11 can be from the end of the belt) at a height above the belt 5 which is preferably in the range 2 to 10 times that of the largest characteristic dimension of the grain of catalyst (its length in the case of an extrudate).

It is possible to position one or more lines 11 in parallel, depending on the width of the transport band and the shape of the line end.

In the case of a spherical line nozzle, the diameter of the nozzle of the line is preferably less than or equal to the largest characteristic dimension of the grain of catalyst.

If the belt allows the simultaneous passage of N particles simultaneously across the width, up to N tubes 11 can be positioned in parallel, each with a valve, the valves being controlled simultaneously or separately by the control means 10 as a function of the number of analysers used in parallel.

It is also possible to operate with a single line 11, but where the end has a rectangular cross section which can generate a blade jet of gas, the thickness of the jet then being preferably less than or equal to the largest characteristic dimension of the grain of catalyst.

In order to take into account the distance between the detection means and the evacuation means, the control system triggers opening-closing cycles with a delay which is a function of the distance to travel between these two points. As an example, if the length of the belt between the focal position of the analyser on the belt 9 and the evacuation means (valve, air injection nozzle 12) is 3 m and the speed of travel on the conveyor belt is 3 m/s, a delay of one second is used, optionally corrected to account for the response time of the analyser 8, the control means 10 or the valve 12.

For the requirements of the invention and in order to be selective, the opening-closing cycle of the valve has to be rapid and consistent with the period of time for the grains to pass in front of the detector. Preferably, the opening-closing cycle time will not exceed 1 to 5 times the time for the grains to pass in front of the detector, preferably less than 3 times this mean passage time.

Thus, the valve and actuator technologies will be selected so as to have an opening-closing cycle in the range 5 to 250 ms depending on the speed of travel of the transport means 5.

The jet of gas (for example air) generated during this period has a speed which is at least equal to 5 times the terminal velocity of fall of the grain of catalyst, preferably 10 times the terminal velocity of fall (in the case of a hydrotreatment extrudate, the terminal velocity of fall is generally close to 5 m/s and in the range 2 to 7 m/s).

When the actuator triggers opening of the valve, the jet of gas deflects the trajectory of the grain of catalyst towards a receptacle 14 which harvests all of the grains to be eliminated containing the unwanted element.

If the actuator is not triggered, then the trajectory of the grain leaving the belt describes a normal parabola which is a function of the speed of travel of the conveyor belt and the terminal velocity of fall of the particles. The grain of catalyst then falls into a receptacle 13 which harvests all of the grains to be eliminated not containing the unwanted element.

Thus, the catalyst collected at 13 will constitute a new batch not containing the unwanted chemical element.

Compared with the prior art, the invention can be used for rapid sorting of at least 20 to 100 objects (grains of catalyst)/second, in general at least 50 or even 100 objects/second, and its use means that up to 1000 objects/second can be processed.

The invention claimed is:

1. A method for separating at least one catalyst from a mixture of homogeneously shaped catalysts, the catalysts being in the form of grains and comprising at least one metal selected from Ni, Co, Mo, and W, the catalyst to be separated comprising W as a characteristic metal and the other catalysts of the mixture containing at least one metal selected from Ni, Co and Mo but not containing said characteristic metal W, said method comprising:
    passing the grains of the catalyst of said mixture in front of a Laser Induced Breakdown Spectroscopy (LIBS) detection system,
    detecting the presence of said characteristic metal in the catalysts by the LIBS, the wavelength of the LIBS being selected so as to detect said characteristic metal, and
    sending a signal from the LIBS detection system to a means for evacuating the grains of catalyst comprising said characteristic metal W in a manner such as to separate said grains comprising said characteristic metal W from the grains of the other catalysts of said mixture containing at least one metal selected from Ni, Co and Mo, but not containing W.

2. The method according to claim 1, in which the other catalysts of the mixture not containing said characteristic metal W include at least one catalyst containing molybdenum.

3. The method according to claim 1, in which the catalyst to be separated comprising W as the characteristic metal also contains Ni, and the other catalysts of the mixture not containing said characteristic metal W include at least one catalyst containing NiMo or CoMo or NiCoMo.

4. The method according to claim 1, in which the catalysts of the mixture are hydrotreatment and/or hydrocracking catalysts.

5. The method according to claim 1, in which the catalysts are spent hydrotreatment and/or hydrocracking catalysts the support of which is constituted by alumina or silica-alumina, with zeolite optionally being present.

6. The method according to claim 1, in which the catalysts are homogeneously shaped.

7. The method according to claim 1, in which the catalysts of the mixture are in the form of cylindrical extrudates.

8. The method according to claim 1, in which the catalysts of the mixture are spent catalysts.

9. The method according to claim 1, in which the time period for one grain to pass in front of the LIBS detection system is less than 50 ms.

10. The method according to claim 1, in which the maximum spacing between the grains, when passing in front of the LIBS, is equal to their largest characteristic dimension.

11. The method according to claim 1, in which the grains, when passing in front of the LIBS, flow in a manner such that they are spaced apart by a distance in the range from zero to their largest characteristic dimension, the measurement frequency being in the range 1/t to 1/2t, t being the period of time for a grain to pass in front of the LIBS detection system.

12. The method according to claim 1, in which the grains are passed in front of the LIBS via a transport means and the LIBS is positioned in a manner such that the depth of the analysis field above the surface of the transport means is in the range 1/3 to 3 times the smallest characteristic dimension of the grain.

13. A device for separating at least one catalyst from a mixture of homogeneously shaped catalysts, the catalysts being in the form of grains, the catalyst to be separated comprising W as a characteristic metal and the other catalysts of the mixture containing at least one metal selected from Ni, Co and Mo but not containing said characteristic metal W, said device comprising:
- a Laser Induced Breakdown Spectroscopy (LIBS) detection system comprising at least one laser in front of which the catalyst grains pass, the detection time for the LIBS being less than 50 ms, and the detecting wavelength of the LIBS being that of the characteristic metal W, at least one analyser (8) and at least one control means (10),
- a line for transporting the grains of the mixture of catalysts in front of the LIBS, the line being provided with a transport means, means for controlling the rate of flow of the grains onto said transport means and means for controlling the speed of said transport means, said transport means being regulated in a manner such that the maximum distance between the grains of catalyst when being transported in front of the LIBS is equal to the largest characteristic dimension of a grain and in that the period of time for a grain to pass in front of the LIBS detection means is less than 50 ms, and
- at least one means for evacuating grains of the catalyst to be separated comprising said characteristic metal W and at least one means for evacuating grains of the other catalysts containing at least one metal selected from Ni, Co and Mo but not containing said characteristic metal W, said means for evacuating grains of catalyst to be separated being actuated from said control means when the characteristic metal is detected by the LIBS.

14. The device according to claim 13, in which the transport means is a ribbed belt, the depth of the ribs being in the range 0.7 to 1.3 times the largest characteristic dimension of the grains.

15. The device according to claim 13, in which the transport means is provided so that the grains flow in a manner such that their spacing is in the range from zero to their largest characteristic dimension, the measurement frequency being in the range 1/t to 1/2t, t being the period of time for a grain to pass in front of the LIBS detection system.

16. The method according to claim 6, in which the catalysts are in the form of cylindrical extrudates, beads, trilobes or multilobes.

17. The method according to claim 1, in which the time period for one grain to pass in front of the LIBS detection system is less than 10 ms.

18. The device according to claim 13, wherein the detection time for the LIBS is less than 10 ms, and the period of time for a catalyst grain to pass in front of the LIBS detection means is less than 10 ms.

19. The device according to claim 13, wherein the device allows for separating at least one catalyst from a mixture of homogeneously shaped catalysts wherein the catalyst are in the form of cylindrical extrudates.

* * * * *